United States Patent [19]
Shillington et al.

[11] Patent Number: 5,616,136
[45] Date of Patent: Apr. 1, 1997

[54] QUICK RELEASE NEEDLE REMOVAL APPARATUS

[75] Inventors: Richard A. Shillington, Leucadia; Kenneth R. McCord, Encinitas; Gary H. Sanders, Margaratia, all of Calif.

[73] Assignee: Med-Safe Systems, Inc., Oceanside, Calif.

[21] Appl. No.: 370,241

[22] Filed: Jan. 9, 1995

[51] Int. Cl.⁶ ............................................. A61M 5/00
[52] U.S. Cl. ................................. 604/240; 604/187
[58] Field of Search ............................. 604/205, 110, 604/218, 242, 224, 206, 187, 240, 241, 243; 279/60, 64

[56] References Cited

U.S. PATENT DOCUMENTS

| | | | |
|---|---|---|---|
| 1,683,350 | 9/1928 | Hein . | |
| 1,985,586 | 12/1934 | Stone | 279/60 |
| 2,159,593 | 5/1939 | Scrimgeour | 604/242 |
| 2,727,514 | 12/1955 | Lockhart | 604/242 |
| 3,063,450 | 11/1962 | Myerson et al. | 128/218 |
| 3,179,107 | 4/1965 | Clark | 604/242 |
| 4,490,142 | 12/1984 | Silvern | 604/241 |
| 4,740,205 | 4/1988 | Seltzer et al. | 604/241 |
| 4,768,568 | 9/1988 | Fournier et al. | 141/286 |
| 4,892,016 | 1/1990 | Anderson | 279/64 |
| 5,000,744 | 3/1991 | Hoffman et al. | 604/232 |
| 5,002,537 | 3/1991 | Hoffman et al. | 604/232 |
| 5,062,837 | 11/1991 | Al-Sioufi et al. | 604/240 |
| 5,069,225 | 12/1991 | Okamura | 604/240 |
| 5,217,025 | 6/1993 | Okamura | 128/765 |

*Primary Examiner*—Corrine M. McDermott
*Attorney, Agent, or Firm*—Baker, Maxham, Jester & Meador

[57] ABSTRACT

A quick release needle holder, comprises a tubular barrel having a needle receiving socket on one end, the needle receiving socket having a segmented wall defining a plurality of annular jaws having internal threads, a device for normally biasing the jaws into an inner position for threadably receiving a needle hub, and a device for releaseably biasing said jaws to a needle hub releasing position.

19 Claims, 5 Drawing Sheets

5,616,136

QUICK RELEASE NEEDLE REMOVAL APPARATUS

BACKGROUND OF THE INVENTION

The present invention relates to needle removal devices for syringes and other holders and pertains particularly to an improved extractor for quick and easy removal of needles from holders.

A huge volume of hypodermic needles are used daily in the medical and health care industry and must be disposed of safely. These used needles pose a major health problem to the medical personnel using them as well as others who may come into contact with them. The safe and effective disposal of these hypodermic needles poses one of the greatest disposal problems for the medical and health care industry.

Hypodermic needles are widely used for both injection of medication and for withdrawing blood samples for diagnostic purposes. In many instances the needle is removed from the holder and disposed of separately from the holder. In some cases, particularly with certain blood drawing devices, the holder is reused. In these cases, it is essential that the needle be easily, quickly and safely removed without risk to the user.

The typical hypodermic needle comprises an elongated thin cannula having a sharp tip on one end and a hub at or near the other end for detachable attachment to a holder. The hub may have a threaded screw connector, Luer lock, or other type connector. The needle is usually covered with a protective tube or sheath detachably coupled to the hub to aid in connecting the needle to the holder. The protective sheath is removed when the needle is to be used. The sheath may be used to protectively cover the needle after use. However, attempts to reinsert the needle into the sheath often result in pricks of the skin of the user.

The present common technique of drawing blood samples is by means of an evacuated tube and holder combination such as that sold under the trademark VACUTAINER by the Becton Dickinson Company. These blood collection assemblies comprise a tubular holder or barrel having a double needle in one end and receives an evacuated tubular chamber. The needle is threadably mounted in one end of the tubular holder with an exterior needle for penetrating the patient tissue for receiving blood. The interior needle is covered with a sheath valve and penetrates an elastomeric stopper in one end of a vacuum tube which acts to draw the blood.

Many devices have been proposed in the past for removal and disposal of the needles. Examples of these are disclosed in the following patents:

| | |
|---|---|
| Shillington | 4,667,821 |
| Shillington | 4,984,686 |
| Thead et al. | 4,986,811 |
| Sagstetter et al. | 5,086,922 |
| Sagstetter et al. | 5,092,462 |
| Shillington | 5,249,680 |

These prior art devices are generally effective to remove the needles. However, they all have various drawbacks for example, most of them require the use of both hands.

It is desirable that a simple, safe and effective quick release needle holder for hypodermic needles be available.

SUMMARY OF THE INVENTION

It is the primary object of the present invention to provide a simple and effective quick release needle holder for hypodermic needles.

In accordance with a primary aspect of the present invention, a quick release needle holder for hypodermic needles, comprises a tubular barrel having a needle hub receiving socket on one end, said needle receiving socket having a segmented wall defining a plurality of inwardly directed annular jaws or receiving and gripping a needle hub means for normally biasing said jaws inwardly to an innermost position for gripping and mounting a needle hub; and means for releasably biasing said jaws to a needle hub releasing position.

BRIEF DESCRIPTION OF THE PREFERRED EMBODIMENTS

The above and other objects and advantages of the present invention will become apparent from the following description when read in conjunction with the accompanying drawings wherein.

DETAILED DESCRIPTION OF THE PREFERRED EMBODIMENTS

Figure 1:
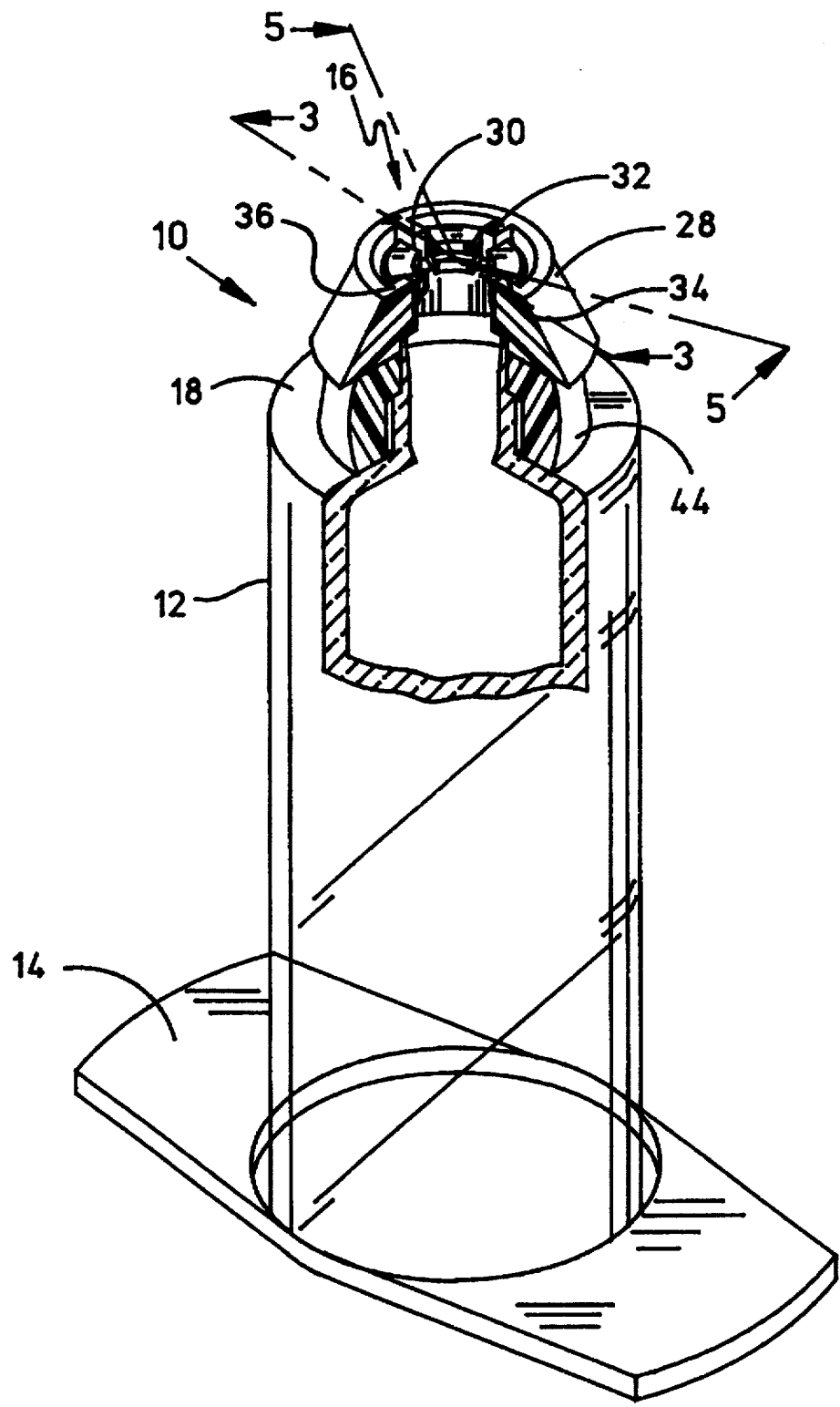
FIG. 1 is a perspective view of a preferred embodiment of the invention with portions broken away to reveal details.

Referring to FIG. 1 of the drawings an exemplary embodiment of the invention embodied in a holder of a blood collection assembly is illustrated. The blood collection assembly comprises a generally cylindrical tube 12 having finger flanges 14 on an open end and a neck including a needle hub mounting socket designated generally by the numeral 16 on the other end. The present invention was devised specifically for blood collection assemblies but is applicable to other hypodermic needle holders such as syringes, IV tubing site connectors and the like.

As illustrated in FIGS. 1–3 and 4, the tube or holder has a forward end-wall 18 with a reduced needle hub mounting socket formed of a reduced forwardly projecting neck or annular wall portion that is segmented into four segments 20, 22, 24 and 26. These segments define a plurality of inwardly directed annular jaw members 20, 22, 24 and 26 which form a socket for threadably receiving and mounting a needle hub. The jaw members are formed with internal threads 38 for threadably receiving the threaded hub of a needle. The jaws extend coaxially and are annularly spaced about the central longitudinally axis of the barrel 12. The jaws are further mounted to pivot inwardly and outwardly toward and away from the central axis for gripping and releasing a threaded hub of a needle, respectively. The slots (FIG. 3) between the jaws are formed of outermost opposed surfaces 40 tapered inward from the outer end to inner opposed surfaces 42 forming a straight portion at the inward or innermost portion.

Figure 2:
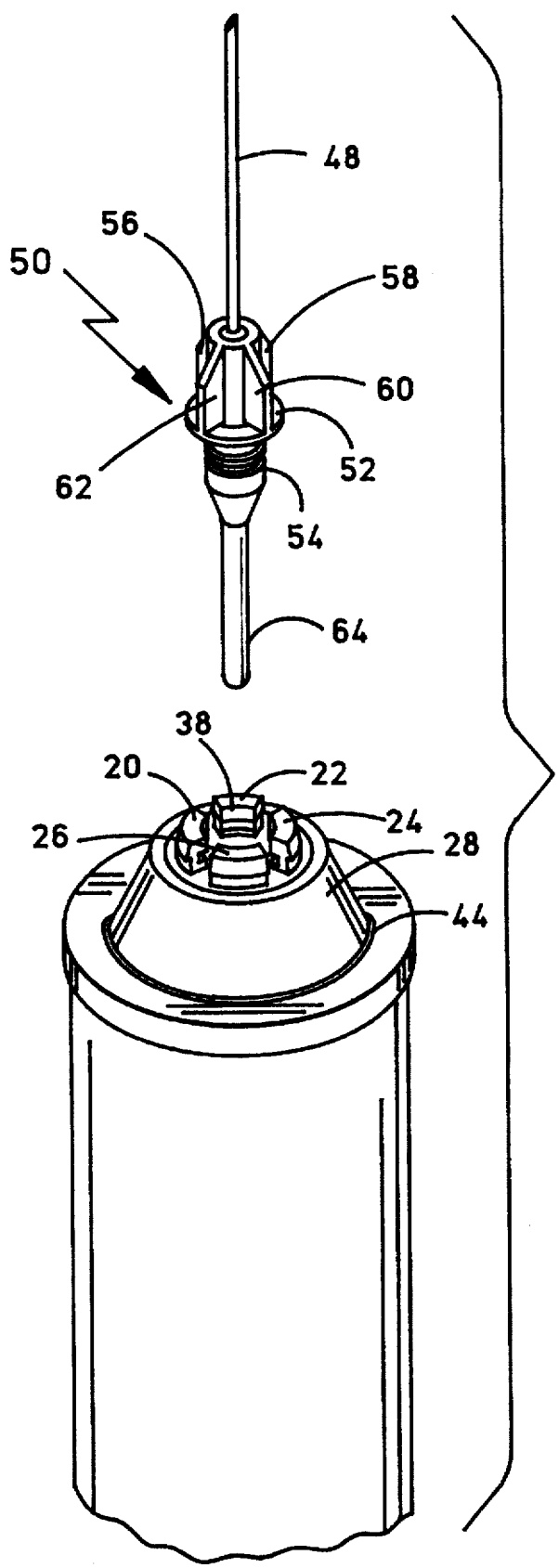
FIG. 2 is a an exploded view showing the holder socket in the ejection position with a needle shown adjacent the socket.
Figures 3, 4, 5:
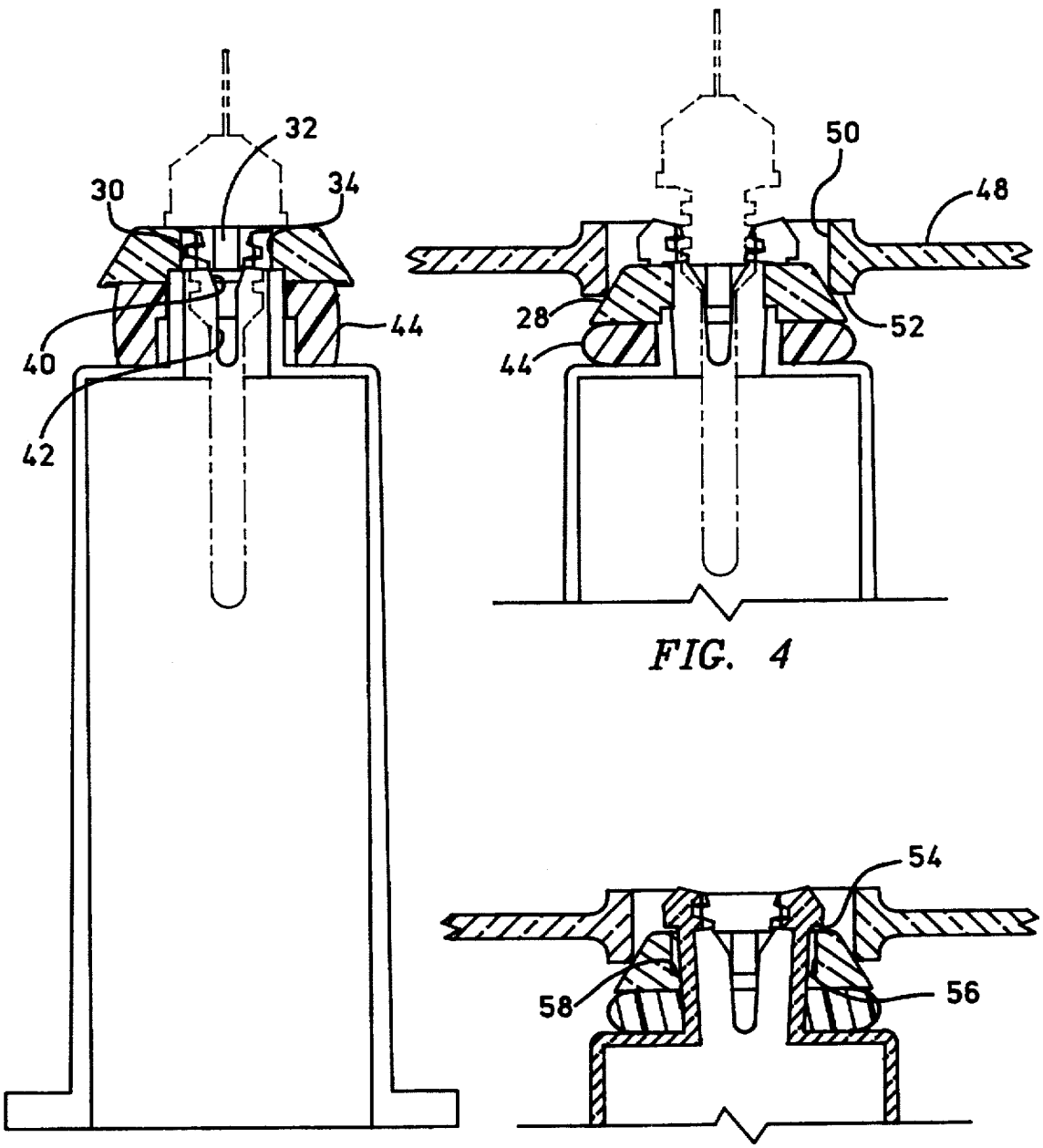
FIG. 3 is a section view taken generally on line 3—3 of FIG. 1.
FIG. 4 is a section view like FIG. 3 showing the needle holder in the ejection position.
FIG. 5 is a section view like FIG. 4 taken generally on line 5—5 of FIG. 1.

A longitudinally slidable collet 28 is mounted on and extends around the jaw members 20–26 and is slideably mounted for axial reciprocal movement thereon. The collet includes inwardly extending wedge members 30, 32, 34 and 36 which extend into the slots formed by surfaces 40 and 42 between the respective jaws 20–26. The wedge members 30–36 act as cam means for camming engagement with surfaces 40 and 42 of the slots between the jaw members for biasing them outwardly into a needle hub releasing position, as shown in FIGS. 2 and 4. The collet is normally biased to a forwardmost position by an elastic collar 44, as shown in FIGS. 1 and 3 for retaining the jaws in an innermost position for threading engagement with the hub of the needle.

The connector assembly is designed to threadably receive or grip the threaded hub of a needle of the type as shown in FIG. 2. The collet 28 is normally biased to the forwardmost position by means of a silicone collar or spring 44 so that the jaws can threadably receive the hub of the needle. The collet may be biased to the rearmost position as shown in FIGS. 2 and 4 to cam the jaws open and release the hub of the needle.

Referring to FIG. 2 the needle connector assembly is designed to mount and retain a conventional needle assembly as illustrated. The needle has an elongated hollow cannula 48 which is mounted to and extends to both directions from a hub designated generally by the numeral 50 which comprises a central radially extending disk like flange 52 with a threaded stud like member 54 extending therefrom. A splined or fluted coupling is formed on the forward end of the needle assembly comprising radially extending splines or ribs 56, 58, 60 and 62. The cannula has an outer or external needle and an inner or internal needle which is covered by a silicone sheath 64 which forms a valve.

The needle is mounted in the retainer and connector assembly by threadably extending the needle hub assembly into the socket. The needle flange 52 engages the outer ends of the jaws and stops or positions the threaded portion 54. Release of the collet permits the spring to force the collet forward forcing the jaws to their inner gripping position for gripping or threadably receiving the hub of the needle assembly. This positions the inner needle inside the tube 12 to be engaged and to puncture a stopper of a vacuum blood collection tube.

When it is desired to remove the needle, the collet is simply moved backward to the position as shown in FIGS. 2, 4 and 5 biasing the jaws open releasing the needle hub for its removal. This is preferably accomplished by means of an annular shoulder surrounding an aperture or opening in a disposable container, as shown in FIGS. 4 and 5 so that the needle is quickly released and falls directly into the disposable container. As shown in FIGS. 4 and 5, a disposable container wall 48 is provided with an aperture 50 having a surrounding annular shoulder 52. The collet 28 is engaged with shoulder 52 and the holder pushed axially forward. This forces the collet backward as shown against elastic collar 44 and cams the jaws 20–26 open allowing the needle to fall from the socket.

Referring to FIG. 5, further details of the jaws show a shoulder 54 on the back surface of each jaw. The collet 28 has a recess 56 that receives the shoulder 54 and a shoulder 58 which engages it when in the forward position. This construction retains the collet on the jaws and retains the jaws in the inner closed position.

Figures 6, 7, 8:
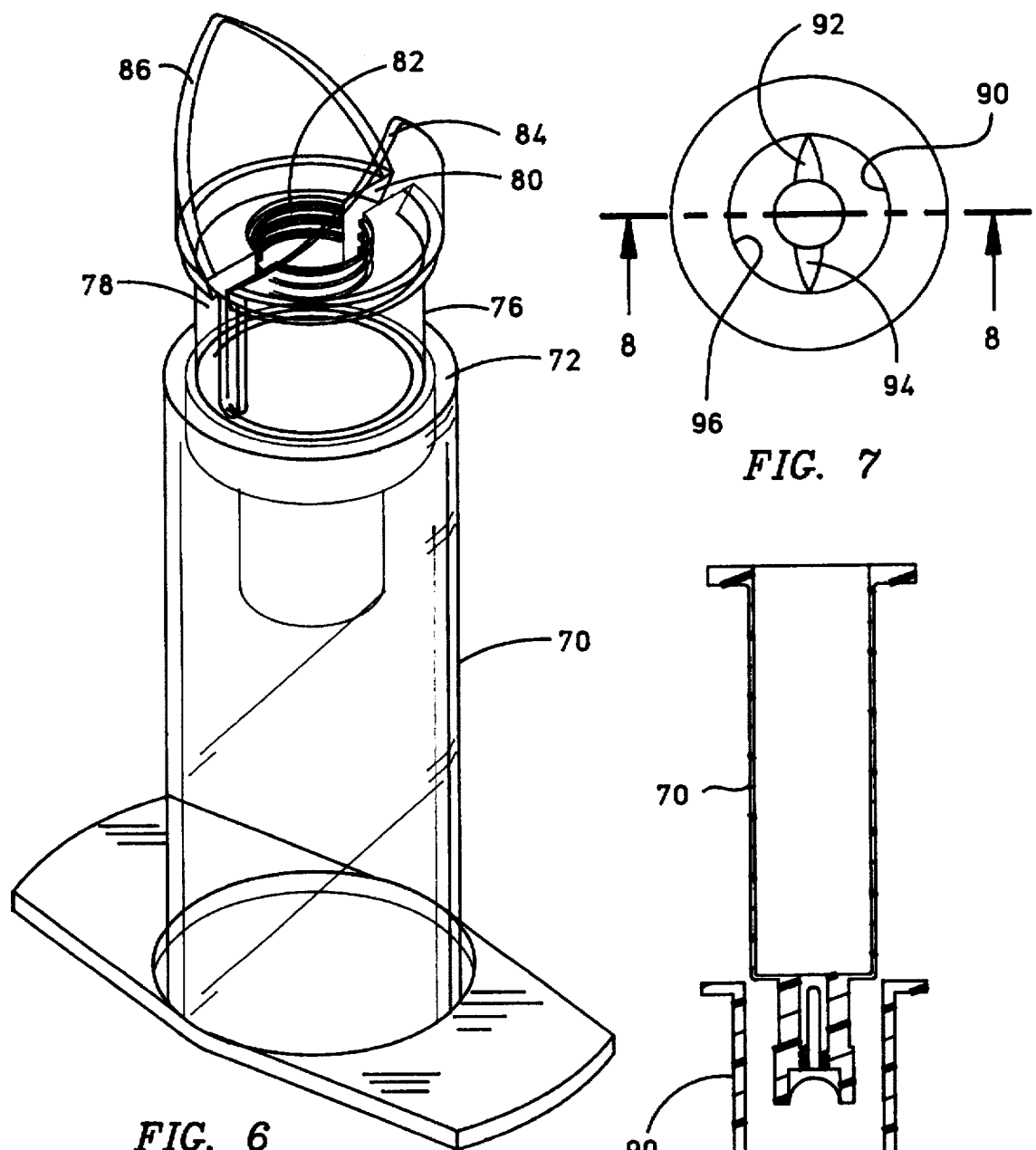
FIG. 6 is a perspective view of an alternate embodiment of the invention with portions broken away to reveal details.
FIG. 7 is a top plan view of an ejector receptacle for the holder of FIG. 6.
FIG. 8 is a side elevation view in section showing the needle holder positioned for insertion in the ejector.

Referring to FIG. 6, an alternate embodiment of the invention is illustrated wherein the blood collection holder comprises a barrel 70 having a forward end wall 72 from which projects a connector assembly comprising an annular forwardly extending wall, formed by two opposing segments defining opposed retainer jaws 76 and 78, respectively. The jaws are formed with an inner semicircular threaded surface 80 and 82, which contain thread portions as illustrated for threadably receiving the threaded hub of a needle. The jaw members are preferably designed to be normally biased to the innermost position as illustrated for threadably receiving the threaded hub of a hypodermic needle. Thus, the needle may be threadably mounted into the assembly as illustrated in prior embodiments.

Referring to FIGS. 7 and 8, a quick release device is provided in the form of a cam device for camming the jaws open to release the needle. The cam device comprises a cylindrical receptacle 90 which may be formed in a wall of a disposable container or as an insert for a container. The tube-like receptacle has a diameter to receive a holder 70 and a pair of wedge cams 92 and 94 at an inner end adjacent and on opposite sides of an aperture 96 for a needle to pass.

When it is desired to remove the needle, the holder is aligned with the receptacle as shown in FIG. 8 and inserted into the receptacle to engage the two cams. Tapered guides 84 and 86 are provided on the forward end of the jaw members 76 and 78 to enable quick and easy alignment of the cam member's with the slots separating the jaws 76 and 78. Engagement of the slots with these wedges and forcing the holder downward into engagement with the cams or wedges, cams the jaws to an open position releasing the hub of the needle assembly. The needle assembly then falls out of the socket through aperture 96 into the container.

Figure 9:
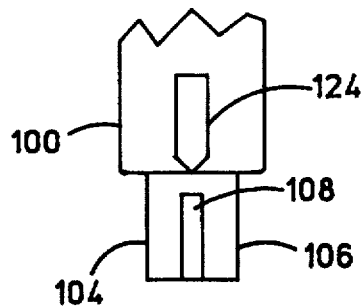
FIG. 9 is a side elevation partial view of a further embodiment of the invention.
Figure 10:
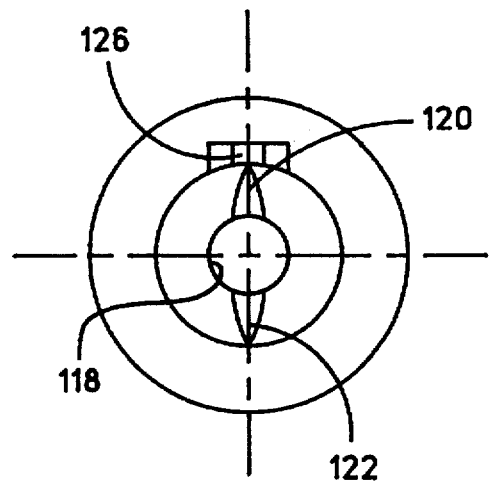
FIG. 10 is a top plan view of an ejector receptacle for the holder of FIG. 9.
Figure 11:
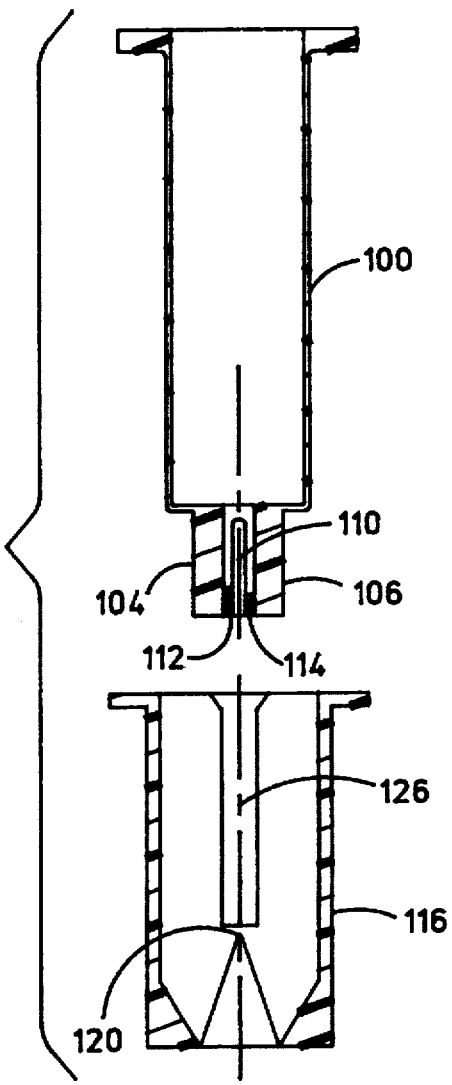
FIG. 11 is a side elevation view in section showing the needle holder of FIG. 9 positioned for insertion in the ejector receptacle of FIG. 9.

Referring to FIGS. 9–11, a further embodiment of the invention is illustrated wherein guide or orientation means are on the side of the barrel and receptacle. This eliminates the forward projection and keeps the barrel or holder conventional size. In this embodiment a barrel 100 of a holder is provided with a forwardly extending necked down annular wall formed of segments 104 and 106, separated by slots 108 and 110. These segments are, as in the previous embodiments, provided with internal threads 112 and 114 for threadably receiving the threaded hub of a needle. The segments define jaws that are connected or formed in the forward end of the barrel and normally positioned in the innermost position. They may be slightly tilted or cammed outward to the outermost position to release the threaded hub of a needle.

Referring to FIGS. 10 and 11, a needle releasing device in the form of a tubular receptacle 116 is provided as an insert or molded into a wall of a disposable container. The receptacle has an elongated bore to receive the barrel of the needle holder with an aperture 118 and wedge shaped cams 120 and 122 at each side for engaging the slots 108 and 110 for camming the jaws outward to release the needle. The holder barrel 100 is provided with a raised guide rib or projection 124 which cooperatively engages a guide slot 126 in the side of the receptacle 116. This guides and aligns the cams with the slots for camming the jaws open to release a needle into a container (not shown). The rib and guide slot may be of any desired width. The rib may also be of any suitable length. Also, its function may also be achieved by any suitable projection such as a small pin or knob.

The guide slot and rib may also be eliminated in some instances. The ends of slots 108 and 110 engaging the upper edge of cams 120 and 122 can act as detents aligning the slots and cams.

While we have illustrated our invention by means of specific embodiments, it is to be understood that numerous changes and modifications may be made therein without departing from the spirit and scope of the invention, as defined in the appended claims.

We claim:

1. A quick release needle holder for hypodermic needles comprising:
    a tubular barrel having an end and a needle hub receiving socket on said end for receiving a needle hub;
    a needle hub receiving socket having a segmented wall defining a plurality of inwardly directed annular jaws for receiving and gripping said needle hub;
    means for normally biasing a jaws inwardly to an innermost position for gripping and mounting said needle hub; and
    means for releasably biasing said jaws to a needle hub releasing position comprising cam means slidable axially along said jaws.

2. A needle holder according to claim 1 wherein said jaws have an outer surface and said means for normally biasing said jaws inwardly to an innermost position for gripping a needle hub comprises a collet biased axially along said outer surface of said jaws.

3. A needle holder according to claim 2 wherein said cam means is carried by said collet.

4. A needle holder according to claim 2 wherein said jaws are formed with threads for threadably engaging threads on said needle hub.

5. A needle holder according to claim 1 wherein said segmented wall is divided into four segments.

6. A needle holder according to claim 5 wherein said cam means extends between said segments.

7. A needle holder according to claim 1 wherein said means for releasably biasing said jaws to a needle hub releasing position comprises a disposal container having a wall and said cam means on said disposal container wall, said cam means slidable axially along said jaws.

8. A needle holder according to claim 7 wherein said segmented wall is divided into two segments.

9. A needle holder according to claim 8 wherein said segmented wall segments have an outer end and are formed with guide means at said outer end.

10. A needle holder according to claim 1 wherein said jaws are formed with threads for threadably engaging threads on said needle hub.

11. A quick detach needle hub connector assembly, comprising:
    a generally cylindrical tubular barrel having an axis, an end and a needle hub connector integral with said tubular barrel on said end for receiving a needle hub;
    said needle hub connector comprising a needle hub receiving socket defined by an annular wall divided by slots into segments defining a plurality of jaws moveable inwardly toward said axis and having an outer surface;
    retaining means for normally biasing and retaining said jaws into an innermost position for gripping and mounting a needle hub; and
    biasing means comprising cam means slidably axially along said jaws for biasing said jaws to a needle hub releasing position.

12. A connector assembly according to claim 11 wherein said retaining means comprises a collet biased axially along said outer surface of said jaws.

13. A needle holder according to claim 11 wherein said cam means is carried by said collet.

14. A needle holder according to claim 11 wherein said segmented wall is divided into four segments.

15. A needle holder according to claim 11 wherein said cam means extends between said segments.

16. A needle holder according to claim 11 wherein said means for biasing said jaws to a needle hub releasing position comprises a disposal container having a wall and said cam means on said disposal container wall, said cam means slidable axially along said jaws.

17. A needle holder according to claim 16 wherein said socket wall is divided into two segments having internal threads.

18. A needle holder according to claim 17 wherein said segmented wall segments have an outer end and are formed with guide means at said outer end.

19. A needle holder according to claim 11 wherein said jaws are formed with threads for threadably engaging threads on said needle hub.

* * * * *

UNITED STATES PATENT AND TRADEMARK OFFICE
CERTIFICATE OF CORRECTION

PATENT NO. : 5,616,136
DATED : April 1, 1997
INVENTOR(S) : Shillington et al.

It is certified that error appears in the above-indentified patent and that said Letters Patent is hereby corrected as shown below:

column 5, line 23, change "a" (first occurrence) to -- said --
column 5, line 25, change "said" to --a--
column 5, line 26, change "a" to -- said --
column 5, line 27, change "said" to --a--

Signed and Sealed this

Twenty-ninth Day of July, 1997

Attest:

BRUCE LEHMAN

*Attesting Officer*  *Commissioner of Patents and Trademarks*